US011215687B2

(12) United States Patent
Froidevaux et al.

(10) Patent No.: US 11,215,687 B2
(45) Date of Patent: Jan. 4, 2022

(54) MAGNETIC RESONANCE IMAGING METHOD WITH HYBRID FILLING OF K-SPACE

(71) Applicants: ETH Zurich, Zurich (CH); UNIVERSITAET ZUERICH, Zurich (CH)

(72) Inventors: Romain Froidevaux, Zurich (CH); Markus Weiger, Zurich (CH)

(73) Assignees: ETH Zurich, Zurich (CH); UNIVERSITAET ZUERICH, Zurich (CH)

(*) Notice: Subject to any disclaimer, the term of this patent is extended or adjusted under 35 U.S.C. 154(b) by 0 days.

(21) Appl. No.: 16/754,147

(22) PCT Filed: Oct. 8, 2018

(86) PCT No.: PCT/EP2018/077361
§ 371 (c)(1),
(2) Date: Apr. 7, 2020

(87) PCT Pub. No.: WO2019/072778
PCT Pub. Date: Apr. 18, 2019

(65) Prior Publication Data
US 2020/0363484 A1 Nov. 19, 2020

(30) Foreign Application Priority Data
Oct. 9, 2017 (EP) ..................... 17195568

(51) Int. Cl.
*G01R 33/48* (2006.01)
*A61B 5/055* (2006.01)
*G01R 33/561* (2006.01)

(52) U.S. Cl.
CPC .......... *G01R 33/4822* (2013.01); *A61B 5/055* (2013.01); *G01R 33/4816* (2013.01); *G01R 33/5618* (2013.01)

(58) Field of Classification Search
CPC ............ G01R 33/4816; G01R 33/4822; G01R 33/5618; A61B 5/055
See application file for complete search history.

(56) References Cited

U.S. PATENT DOCUMENTS

| 8,878,533 B2 | 11/2014 | Grodzki et al. |
| 2008/0068016 A1* | 3/2008 | Gaddipati .......... G01R 33/4824 324/318 |

(Continued)

OTHER PUBLICATIONS

Romain Froidevaux et al, "Filling the dead-time gap in zero echo time MRI: Principles compared", Magnetic Resonance in Medicine 79:2036-2045 (online: Aug. 30, 2017, paper copy).

(Continued)

*Primary Examiner* — Gregory H Curran
(74) *Attorney, Agent, or Firm* — Agris & von Natzmer LLP; Joyce von Natzmer

(57) ABSTRACT

A method for generating an image data set of an image area located in a measurement volume of a magnetic resonance system comprising a gradient system and an RF transmission/reception system, comprises the following method steps: —reading out k-space corresponding to the imaging area, by: (a) activating a frequency encoding gradient in a predetermined spatial direction and with a predetermined strength $G_0$ by means of said gradient system, (b) after the activated frequency encoding gradient achieves its strength $G_0$, radiating a non-slice-selective RF excitation pulse by means of said RF transmission/reception system, (c) after a transmit-receive switch time $\Delta t_{TR}$ following the radiated excitation pulse, acquiring FID signals with said RF transmission/reception system and storing said FID signals as raw data points in k-space along a radial k-space trajectory that is predetermined by the direction and strength $G_0$ of the frequency encoding gradient, (d) repeating (a) through (c) with respectively different frequency encoding gradient directions in each repetition until k-space corresponding to the image area is read out in an outer region of k-space along radial k-space trajectories, said radial k-space trajectories each having a radially innermost limit $k_{gap}$ which depends on said switch time $\Delta t_{TR}$, (e) reading out a remainder of k-space that corresponds to the imaging area, said remainder being an inner region of k-space not being filled by said first region and including at least a center of k-space, in a read out procedure that is different from (a) through (d), and storing (Continued)

all data points read out in (d) and (e); and —reconstructing image data from the read out data points in k-space by implementing a reconstruction algorithm; In order to constrain image fidelity and optimize scan duration under given circumstances, the inner k-space region is subdivided into a core region and at least one radially adjacent shell region.

14 Claims, 5 Drawing Sheets

(56) References Cited

U.S. PATENT DOCUMENTS

| | | |
|---|---|---|
| 2008/0265885 A1 | 10/2008 | Dannels |
| 2010/0244825 A1* | 9/2010 | Brau ................. G01R 33/5611 324/309 |
| 2017/0261577 A1 | 9/2017 | Smink et al. |
| 2018/0149721 A1* | 5/2018 | Beck ................. G01R 33/5611 |

OTHER PUBLICATIONS

David M. Grodzki et al, "Ultrashort echo time imaging using pointwise encoding time reduction with radial acquisition (PETRA)", Magnetic Resonance in Medicine, vol. 67, No. 2, (Jun. 30, 2011), pp. 510-518.

Hyungseok Jang et al, "Ramped hybrid encoding for improved ultrashort echo time imaging", Magnetic Resonance in Medicine., vol. 76, No. 3, (Sep. 18, 2015), p. 814-825.

M. Weiger et al, "MRI with Zero Echo Time", "Encyclopedia of Magnetic Resonance", (Jun. 15, 2012), Chichester, UK John Wiley & Sons, Ltd.

R. Froideaux et al, Ultra-high-bandwidth, high-resolution MRI of fast relaxing spins Shot-T2 MRI: requirements High resolution. Proc 26th Annual Meeting ISMRM, Honolulu (Apr. 22-27, 2017):4037.

Yaotang Wu et al, "Water- and fat-suppressed proton projection MRI (WASPI) of rat femur bone", Magnetic Resonance in Medicine, vol. 57, No. 3, (Jan. 1, 2007), pp. 554-567.

* cited by examiner

MAGNETIC RESONANCE IMAGING METHOD WITH HYBRID FILLING OF K-SPACE

CROSS-REFERENCE TO RELATED APPLICATIONS

This is the U.S. national stage of International application PCT/EP2018/077361, filed Oct. 8, 2018 designating the United States and claiming priority to European application EP 17195568.5, filed Oct. 9, 2017, both of which are incorporated herein by reference in their entireties.

FIELD OF THE INVENTION

The present invention generally relates to a method of magnetic resonance (MR) imaging. More specifically, it relates to a zero echo time imaging method useful for MRI of tissues with short coherence lifetimes.

BACKGROUND OF THE INVENTION

Direct imaging of tissues with short transverse relaxation times ($T_2$ or $T_2^*$) is interesting both from a scientific and also from a clinical point of view (see [1] and references cited therein). It is known that imaging of samples with relaxation times shorter than a few milliseconds requires specialized imaging methods, which most notably include zero echo time (ZTE) based techniques such as algebraic ZTE, PETRA (Pointwise Encoding Time Reduction with Radial Acquisition) and WASPI (Water And Fat Suppressed Proton Projection MRI) [2-4].

U.S. Pat. No. 8,878,533 B1 is directed to a method for generating an image data set of an image area located in a measurement volume of a magnetic resonance system, the magnetic resonance system comprising a gradient system and an RF transmission/reception system, the method comprising:
  reading out k-space corresponding to the imaging area, by:
  (a) activating a frequency encoding gradient in a predetermined spatial direction and with a predetermined strength $G_0$ by means of said gradient system,
  (b) after the activated frequency encoding gradient achieves its strength $G_0$, radiating a non-slice-selective RF excitation pulse by means of said RF transmission/reception system,
  (c) after a transmit-receive switch time $\Delta t_{TR}$ following the radiated excitation pulse, acquiring FID signals with said RF transmission/reception system and storing said FID signals as raw data points in k-space along a radial k-space trajectory that is predetermined by the direction and strength $G_0$ of the frequency encoding gradient,
  (d) repeating (a) through (c) with respectively different frequency encoding gradient directions in each repetition until k-space corresponding to the image area is read out in an outer region of k-space along radial k-space trajectories, said radial k-space trajectories each having a radially innermost limit $k_{gap}$ which depends on said switch time $\Delta t_{TR}$,
  (e) reading out a remainder of k-space that corresponds to the imaging area, said remainder being an inner region of k-space not being filled by said first region and including at least a center of k-space, in a read out procedure that is different from (a) through (d), and storing all data points read out in (d) and (e); and
  reconstructing image data from the read out data points in k-space by implementing a reconstruction algorithm.

According to the above, the k-space region corresponding to the imaging area is subdivided into an inner region and an outer region, wherein the outer region surrounds the inner region, the inner region containing the center of k-space. Different read out procedures are used in the inner and outer regions. In the outer region, the read out is conveniently done along radial k-space trajectories using a gradient strength $G_0$, whereas in the inner region some different read out procedure is adopted.

According to an advantageous embodiment defined in U.S. Pat. No. 8,878,533 B1, the raw data points in the inner region are acquired as Cartesian raw data. This implementation is generally known as the PETRA technique.

A somewhat different approach is used in the case of WASPI, where the raw data in the inner region are also acquired along radial k-space trajectories, but with a lower gradient strength $G<G_0$. The two datasets, i.e. the inner dataset and the outer dataset are combined with optional linear merging in an overlap region [1].

While the use of algebraic ZTE is favorable at small dead-time gaps, direct measurement of missing data is required when more than 3 Nyquist dwells are missed (a dwell corresponds to the inverse of the imaging bandwidth in time domain or to the inverse of the field of view in k-space). In this case, PETRA is usually preferred over WASPI due to its robustness against short-T2 related artifacts [1]. However, its scan efficiency decreases quickly with gap size.

Accordingly, it would be desirable to provide an improved MR imaging method. It is thus an object of the present invention to provide a zero echo time imaging method useful for MRI of tissues with short coherence lifetimes which can overcome some of the limitations of the presently used methods such as algebraic ZTE, WASPI and PETRA.

SUMMARY OF THE INVENTION

According to the present invention, a method for generating an image data set of an image area located in a measurement volume of a magnetic resonance system comprising a gradient system and an RF transmission/reception system, comprises the following method steps:
  reading out k-space corresponding to the imaging area, by:
  (a) activating a frequency encoding gradient in a predetermined spatial direction and with a predetermined strength $G_0$ by means of said gradient system,
  (b) after the activated frequency encoding gradient achieves its strength $G_0$, radiating a non-slice-selective RF excitation pulse by means of said RF transmission/reception system,
  (c) after a transmit-receive switch time $\Delta t_{TR}$ following the radiated excitation pulse, acquiring FID signals with said RF transmission/reception system and storing said FID signals as raw data points in k-space along a radial k-space trajectory that is predetermined by the direction and strength $G_0$ of the frequency encoding gradient,
  (d) repeating (a) through (c) with respectively different frequency encoding gradient directions in each repetition until k-space corresponding to the image area is read out in an outer region of k-space along radial k-space trajectories, said radial k-space trajectories each having a radially innermost limit $k_{gap}$ which depends on said switch time $\Delta t_{TR}$, (e) reading out a remainder of k-space that corresponds to the imaging area, said remainder being an inner region of k-space not being filled by said first region and including at least a center of k-space, in a read out procedure that is different from (a) through (d), and storing all data points read out in (d) and (e); and reconstructing image data from the read out data points in k-space by implementing a reconstruction algorithm.

By virtue of the fact that the inner k-space region is subdivided into a core region and at least one radially adjacent shell region, with raw data points in the core region being acquired as Cartesian raw data, and raw data points in the shell region being acquired along radial k-space trajectories using a gradient strength G that is smaller than the gradient strength $G_0$, it is possible to optimize image fidelity and scan duration under given circumstances.

The method of the present invention will henceforth be addressed as hybrid filling and abbreviated as "HYFI". The HYFI approach improves scan efficiency at large gaps with minimum loss of image quality.

The method of the present invention can be implemented in a conventional MR imaging apparatus.

According to step c), the acquisition of FID signals is started after a transmit-receive switch time $\Delta t_{TR}$ in order to avoid measurement artifacts. This shall include embodiments using the shortest reasonably possible waiting time given by the switch time of the MRI apparatus, but it shall also include embodiments with a somewhat extended waiting time. In the later cases, there will be an increase of scan time because of the need to recover missing information and signal intensity will be lower due nuclear spin relaxation.

Further details and definitions are given in the section "Theory" further below.

Advantageous embodiments are defined in the dependent claims.

According to one embodiment (claim 2), wherein the boundary $k_{gap}$ subdividing the inner and outer k-space regions is given by the product of bandwidth BW and dead time $\Delta t_0$, wherein the dead time $\Delta t_0$ is given by $\Delta t_{RF}$, which is a part of the RF pulse, particularly half of the RF pulse for symmetric RF pulses, plus the transmit-receive switch time $\Delta t_{TR}$.

According to a further embodiment (claim 3), the core region has an outer limit $k_{core}$ given by $$k_{core} = \frac{\Delta t_0}{\Delta t} \cdot s_{Min}$$

wherein
 the dead time to is given by $\Delta t_{RF}$, which is a part of the RF pulse, particularly half of the RF pulse for symmetric RF pulses, plus the transmit-receive switch time $\Delta t_{TR}$,
 the allowed acquisition duration $\Delta t$ is given by $-T_2 \ln(1-A)$ wherein A is an amplitude parameter selected between 0 and 1.
 the minimum shell thickness $s_{Min}$ is selected to be between 0.1 and 10, preferably between 0.5 and 2, particularly about 1.

With the above definition, one can limit Cartesian acquisition to a small core region and thus allow using the more efficient radial acquisition wherever possible.

According to another embodiment (claim 4), the shell region comprises at least two shell regions ($S_1, S_2, \ldots$), each shell region $S_i$ having a shell thickness $s_i$ given by $$s_i = \frac{\Delta t}{\Delta t_0} \cdot k_{in}$$

each shell region having an inner radius $k_{in}$ defined by the thickness of the next radially inward core or shell region. Starting from the innermost region, i.e. the core region, concentric shell regions are added in an onion-like manner until reaching the boundary between inner k-space region and outer k-space region. In an alternative embodiment (claim 5), the various shell regions are radially overlapping, in which case the signal in the overlap region is subjected to a linear interpolation step.

According to yet another embodiment (claim 6), the reconstruction algorithm comprises a Fourier transformation of the data points.

BRIEF DESCRIPTION OF THE DRAWINGS

The above mentioned and other features and objects of this invention and the manner of achieving them will become more apparent and this invention itself will be better understood by reference to the following description of embodiments of this invention taken in conjunction with the accompanying drawings, wherein.

DETAILED DESCRIPTION OF THE INVENTION

Figure 1:
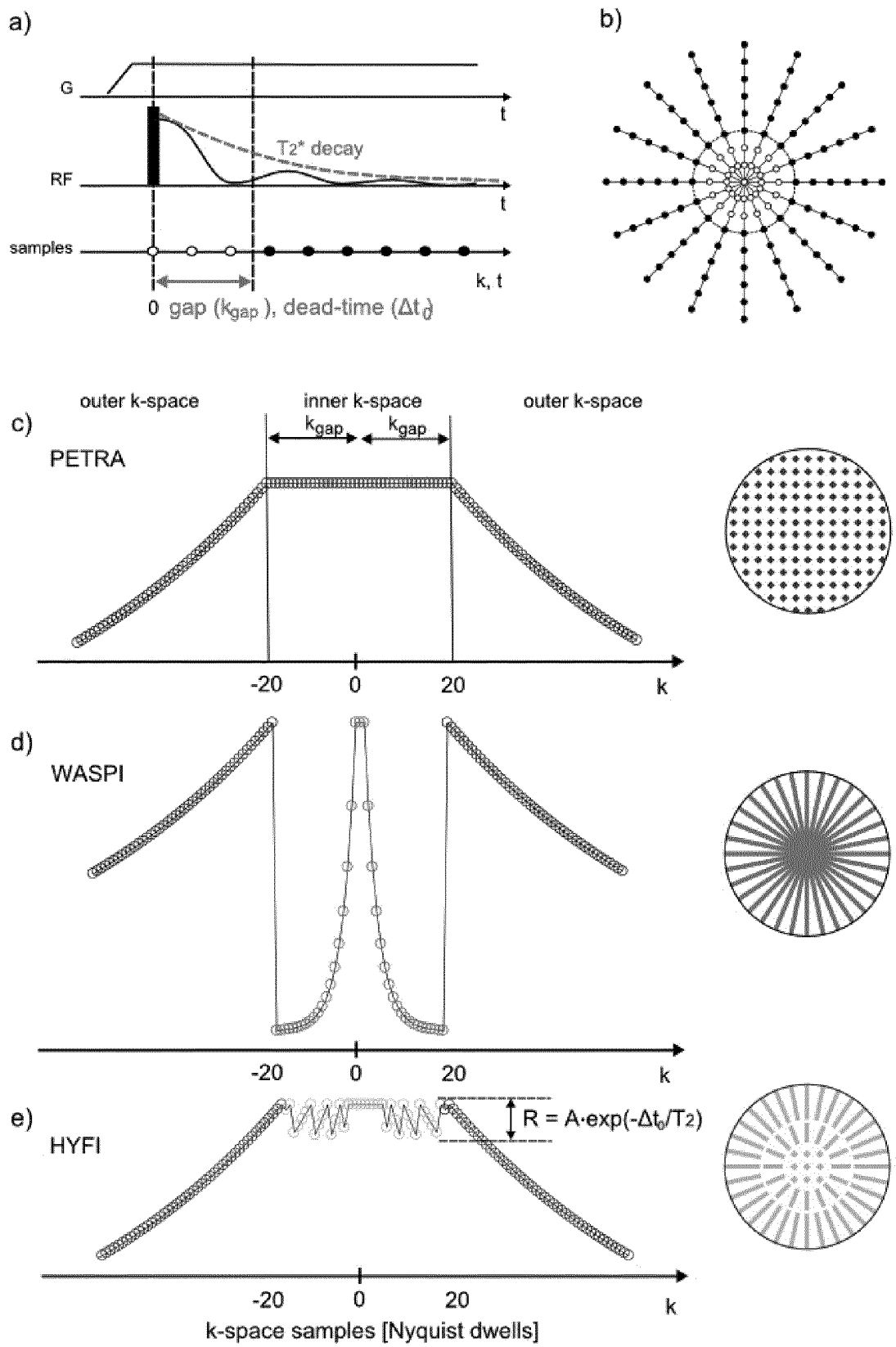
FIG. 1 shows data acquisition in zero echo time-based techniques:
 a) the gradient (G) is ramped up (upper trace) before spin excitation (middle trace); The beginning of the resulting FID cannot be probed due to the dead-time gap ($\Delta t_0$) (white dots in lower trace);
 b) between excitations, the gradient direction is changed slowly to acquire different projections in order to fill the k-space volume of interest;
 c-e) PETRA, WASPI, and HYFI differ in the way they provide the missing data; Left: 1D depiction of k-space T2 weighting; Right: 2D depiction of inner k-space acquisition geometry;
 c) in PETRA, the inner k-space is acquired single-point-wise in a Cartesian fashion leading to constant T2 weighting;
 d) in WASPI, a second set of radial acquisitions is performed at lower gradient strength, giving rise to increased and potentially strong T2 weighting;
 e) HYFI, the method of this invention, is a hybrid between PETRA and WASPI: a combination of Cartesian SPI and multiple sets of radial acquisitions is used to keep the T2 decay in a given range R, wherein R is chosen such as to allow higher scan efficiency with minimum loss of image quality.
Figure 2:
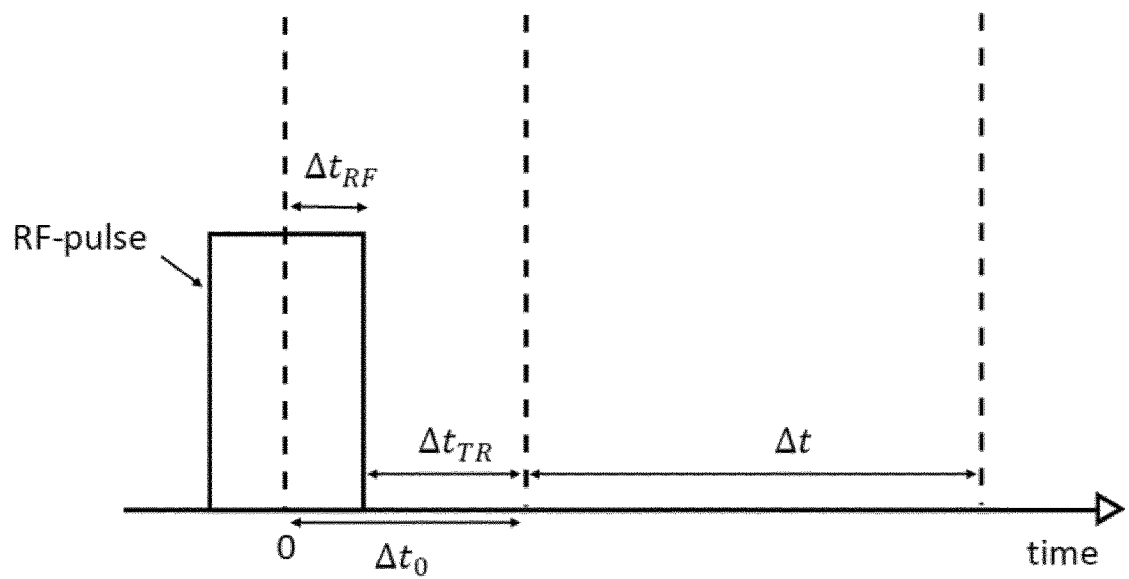
FIG. 2 shows relevant timing intervals in relation to the applied RF pulse; $\Delta t_0$ includes a part of the pulse $\Delta t_{RF}$, half of the pulse duration for symmetric pulses, and the transmit-receive switch time $\Delta t_{TR}$; and $\Delta t$ is the time window corresponding to the acquisition of each shell.

Theory k-Space Acquisition:

The norm of the acquired k-space point $\tilde{k}$ is related to the acquisition time t:

$$\tilde{k}(t,G) = \gamma \cdot G \cdot t \, [m^{-1}] \qquad (1)$$

with γ the gyromagnetic ratio [Hz/T], G the gradient [T/m], t the acquisition time [s]. Moreover, it is useful to express the k-space norm in number of Nyquist dwells (1 dwell has a length of $$\frac{1}{FOV} \, [m^{-1}]$$

with FOV the field of view of the experiment) instead of $[m^{-1}]$. To do so, $\tilde{k}$ should be multiplied by the field of view FOV:

$$k(t,G) = \tilde{k} \cdot FOV = \gamma \cdot G \cdot t \cdot FOV \qquad (2)$$

In PETRA, WASPI and HYFI, acquisition of the outer k-space is performed with a gradient strength $G_0$ and the first data point is sampled at $k_{gap}$, after the dead time $\Delta t_0$:

$$k_{gap} = k(\Delta t_0, G_0) = \gamma \cdot G_0 \cdot \Delta t_0 \cdot FOV \qquad (3)$$

All k-space points smaller than $k_{gap}$ are missed during the acquisition of the outer k-space. However, PETRA, WASPI and HYFI recover the missing data with additional acquisitions performed with lower gradient strengths G (G<$G_0$) such that k-space samples smaller than the gap can be reached after the dead time.

$$k(\Delta t_0, G) < k(\Delta t_0, G_0) = k_{gap} \qquad (4)$$

k-Space T2 Weighting:

Lowering the gradient strength decreases the k-space acquisition velocity $v_k$ which express the number of Nyquist dwells acquired per unit time:

$$v_k = \frac{dk}{dt} = \gamma \cdot G \cdot FOV \, [s^{-1}] \qquad (5)$$

Hence, the k-space regions acquired with a lower gradient strength have a stronger T2 weighting because the amplitude decays faster for a given k-space range.

PETRA vs WASPI:

In PETRA, only one point is acquired per excitation after the dead time $\Delta t_0$ and gradient strengths and amplitudes are changed between each excitation in order to acquire the k-space center on a Cartesian grid. Since all points are measured after the same time, the inner k-space has a constant T2 weighting (FIG. 1c). The number of required excitations to fulfil the Nyquist criterion at the gap evolves with the third power of $k_{gap}$.

$$n_{PETRA} \approx 4/3 \cdot \pi \cdot k_{gap}^3 \qquad (6)$$

In WASPI, several points are measured radially after each excitation. Due to the use of low gradient strengths, the k-space is acquired slowly and a strong T2 weighting appears in the inner k-space. This lead to large amplitude jumps at the gap (FIG. 1d) which in turns gives rise to unwanted point spread function (PSF) side lobes (FIG. 6), see [1]. However timewise, WASPI acquisitions are more efficient than PETRA and especially at large gaps because the number of required excitation evolves with the second power of $k_{gap}$.

$$n_{WASPI} \approx 4 \cdot \pi \cdot k_{gap}^2 \qquad (7)$$

To summarize, the PSF of PETRA is preferred to the PSF of WASPI in view of better image fidelity due to smaller side lobes, but PETRA acquisitions are significantly longer at large gaps.

Detailed HYFI Description:

The goal of HYFI is to optimize scan duration while constraining depiction fidelity.

To this end, a radial acquisition geometry is used whenever possible to optimize scan efficiency but the T2 decay is restricted to a range R (FIG. 1e) to avoid large amplitude jumps and limit PSF side lobes.

Figure 3:
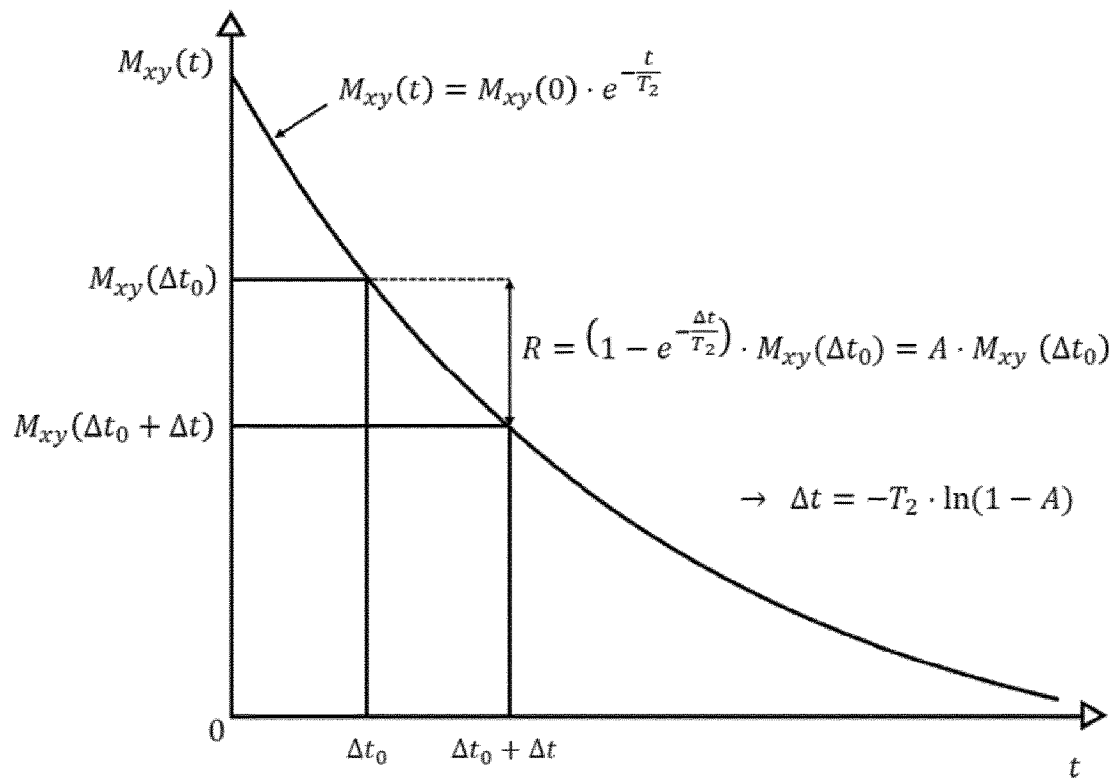
FIG. 3 shows some fundamental relations holding for a given temporal decay of transversal magnetization $M_{xy}(t)$.

The range R is defined proportionally to the amplitude of the transverse magnetization at the dead time $M_{xy}(\Delta t_0)$ (FIG. 3).

$$R = \left[1 - \exp\left(-\frac{\Delta t}{T_2}\right)\right] \cdot M_{xy}(0) \cdot \exp\left(-\frac{\Delta t_0}{T_2^*}\right) = A \cdot M_{xy}(\Delta t_0) \qquad (8)$$

The amplitude factor A corresponds to the proportion of signal amplitude lost during the acquisition duration Δt due to an exponential decay of time constant $T_2$.

Hence, restricting the decay range R amounts to limiting A which is done by limiting the acquisition duration Δt.

Figure 5:
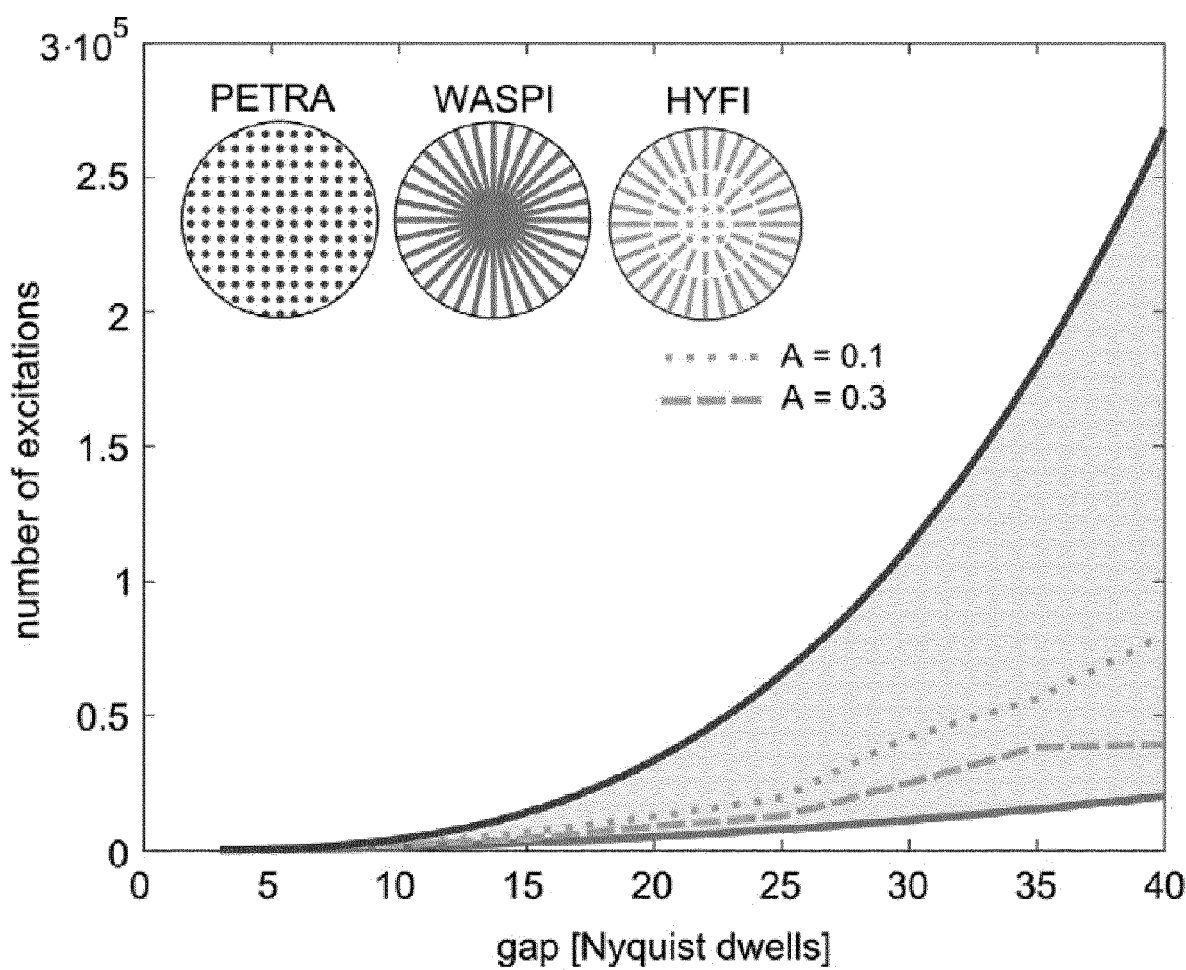
FIG. 5 shows the number of excitations required by each technique to fill the inner k-space, assuming a T2 decay of 64 Nyquist dwells; circles at the top illustrate the acquisition geometries; in 3D, the number of excitations evolves with $k_{gap}^3$ for PETRA and $k_{gap}^2$ for WASPI; in the proposed method, inner k-space is filled by a combination of SPI and radial acquisitions, and thus the green area enclosed by the curves for PETRA and WASPI becomes accessible; green lines represent selected HYFI acquisitions with amplitude coefficients A=0.1 and 0.3.
Figure 6:
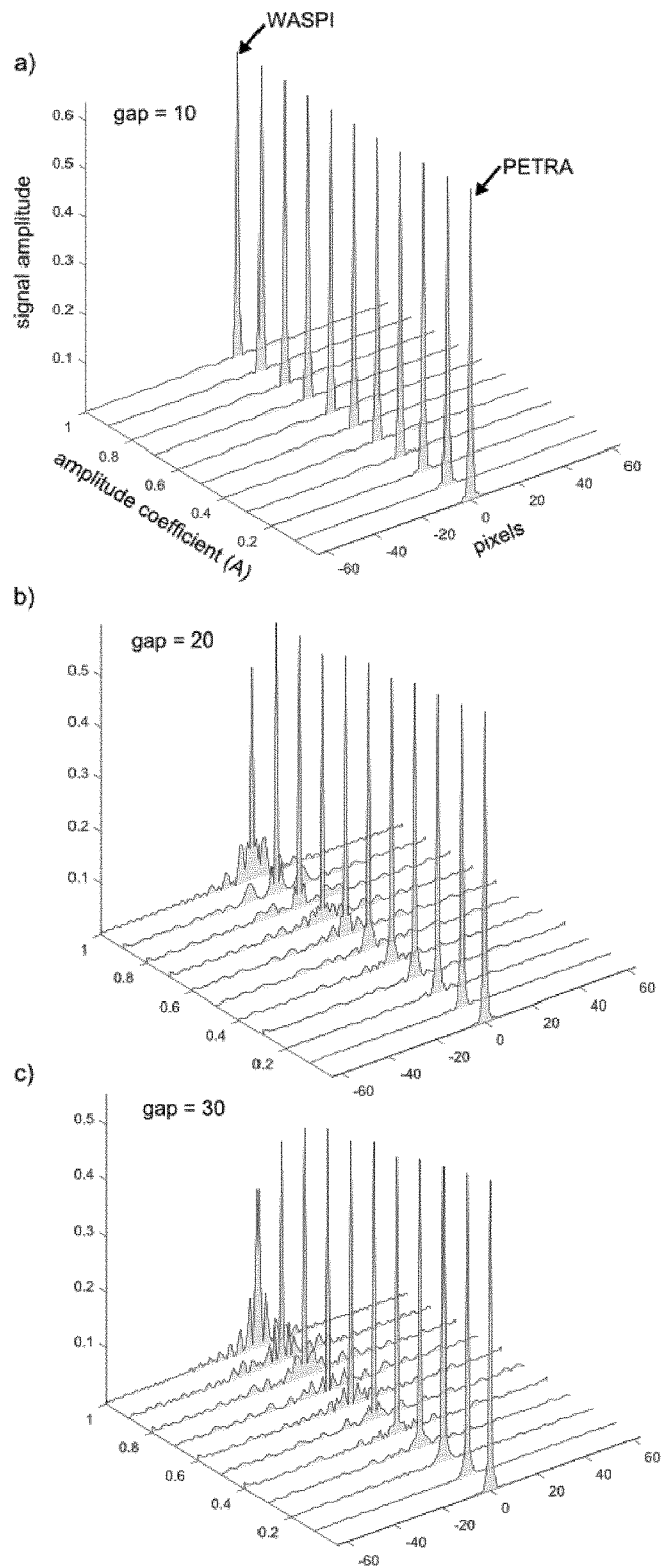
FIG. 6 shows a simulation of point spread functions: 1D HYFI acquisitions were simulated with the following fixed parameters: image matrix size=128, T2=64 Nyquist dwells. PSFs are displayed for different combinations of gap sizes (a-c) and amplitude coefficients A (0=PETRA, 1=WASPI)

Typically, the factor A can be optimized with preliminary acquisitions or simulations as illustrated in FIGS. 5 and 6. In this case, limiting A to 10-30% strongly decreases the number of excitations to be performed and largely preserves the PSF lineshape.

After optimization, the allowed acquisition duration can be calculated as (FIG. 3)

$$\Delta t = -T_2 \cdot \ln(1-A) \qquad (9)$$

However, the allowed acquisition duration may not be long enough to acquire the full inner k-space. Therefore, the inner k-space is split in an onion-like fashion with a core surrounded by one or several shells.

The gradient strength required to reach the core (or $0^{th}$ shell) corresponds to such a low k-space speed that the signal amplitude of the second point would be outside of the allowed range R at the time of its acquisition. Hence, the core is acquired single-pointwise on a Cartesian grid.

Figure 4:
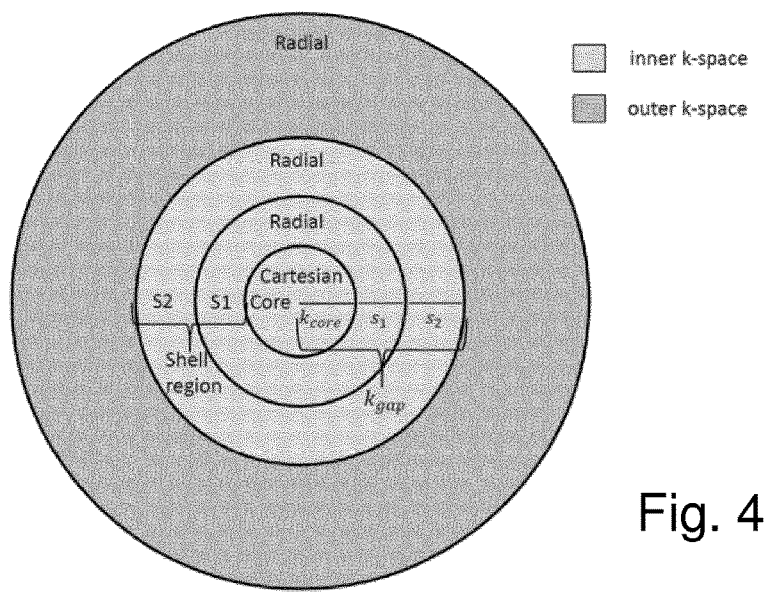
FIG. 4 shows an example of HYFI acquisition wherein the inner region of-k space, of radius equal to the gap, is subdivided into a core region surrounded by two radially adjacent shell regions S1 and S2 of thickness equal to respectively s1 and s2.

On the other hand, in the shells surrounding the core, several points can be measured after each excitation. Thus, in this case, k-space is acquired radially (FIG. 4).

Calculation of Shell Thickness:

The shell thickness, is given by the allowed acquisition duration $\Delta t$ and the k-space acquisition velocity $v_k$.

$$s = \Delta t \cdot v_k = \Delta t \cdot \gamma \cdot G \cdot FOV = \Delta t \cdot BW \quad (10)$$

with BW the imaging bandwidth.

The k-space acquisition velocity, $v_k$, is proportional to the gradient G (Eq. 5) which is determined by the inner radius of the shell, $k_{in}$. The inner radius $k_{in}$ is by definition always acquired after the dead time $\Delta t_0$ and given by:

$$\gamma \cdot G \cdot \Delta t_0 \cdot FOV = k_{in} \quad (11)$$

$$\rightarrow G = \frac{k_{in}}{\gamma \Delta t_0 FOV} [T/m] \quad (12)$$

From Equ. 11 and Equ. 12, we can rewrite the shell thickness, s, as follow $$s = \frac{\Delta t}{\Delta t_0} \cdot k_{in} \quad (13)$$

Note: shell thickness increases linearly with inner radius $k_{in}$.

HYFI Step by Step:
1) Define targeted transverse relaxation time T2
2) Define maximum allowed decay range R within the shell (optimize amplitude parameter A).
3) Calculate maximum acquisition duration $$\Delta t = -T_2 \cdot \ln(1-A)$$

4) Define $s_{Min}$, the minimum shell thickness required to do radial acquisitions. Generally, $s_{Min}$ is selected to be between 0.1 and 10, preferably between 0.5 and 2, and is typically chosen to be 1.
5) Calculate core radius, $k_{core}$, delimiting the boundary between SPI and radial acquisitions.

$$\text{Acquisition geometry} = \begin{cases} \text{Cartesian } SPI, & k \leq k_{core} \\ \text{radial}, & k > k_{core} \end{cases}$$

$$k_{core} = \frac{\Delta t_0}{\Delta t} \cdot s_{Min}$$

6) Calculate inner radius $k_{in_j}$ and outer radius $k_{out_j}$ for each shell j.

$$k_{in_1} = k_{core}$$

$$s_j = \frac{\Delta t}{\Delta t_0} \cdot k_{in_j}$$

$$k_{out_j} = k_{in_j} + s_j$$

$$k_{in_{j+1}} = k_{out_j} + \delta k \text{ with } 0 \leq \delta k \leq 1 \text{ and } \{\forall j | k_{in}j < k_{gap}\}.$$

Note:
if $\delta k=0$, Nyquist criterion is fulfilled everywhere.
If $\delta k=1$, Nyquist criterion is not strictly fulfilled at shell boundaries.
As an option, it would also be possible to linearly merge shells over an overlap region in order to decrease irregularities in the k-space weighting.

7) Calculate k-space directions
  a. SPI
    i. All k-space point on Cartesian grid fulfilling $$|k| \leq k_{core}$$

b. Radial
    i. Calculate number of shots (or radial spokes) to fulfill Nyquist criterion on the outer surface of each shell j $$n = 4 \cdot \pi \cdot k_{out_j}^2$$

ii. Calculate the directions of each shot by spreading these points on the surface of each shell following a suitable trajectory with approximately equal density.
8) Measure data on calculated trajectory
9) Reconstruct image Concluding Remarks FIG. 5 illustrates the scan efficiency of the different methods. At large gaps, the number of excitations required to fill the inner k-space is significantly larger in PETRA ($4/3 * \pi * k_{gap}^3$) than in WASPI ($4*pi*k_{gap}^2$). In HYFI, relatively low amplitude coefficients (0.1 to 0.3) allow significant reduction of the number of excitations compared to PETRA while preserving satisfactory PSF lineshapes (FIG. 6). For example, at a gap of 30 Nyquist dwells and a T2 of 64 Nyquist dwells, the use of HYFI with A=0.3 reduces the number of shots required to fill the inner k-space by almost 80% (from $1.15 \cdot 10^5$ to $2.45 \cdot 10^4$). Assuming repetition times between 1 and 10 ms, this leads to a net gain of 1.5 to 15 minutes per scan.

The HYFI method is evaluated with 1D simulations of point spread functions (PSF), see FIG. 6.

One-dimensional point spread functions (PSF) were simulated by application of the following formula:

$$P = F \cdot T \cdot E \cdot \delta_0$$

wherein F is the pseudo inverse of the encoding matrix E, T is the T2 weighting matrix (T2=64 Nyquist dwells) and $\delta_0$ is the Kronecker delta function located in the center of the field of view.

EXAMPLE

Figure 7:
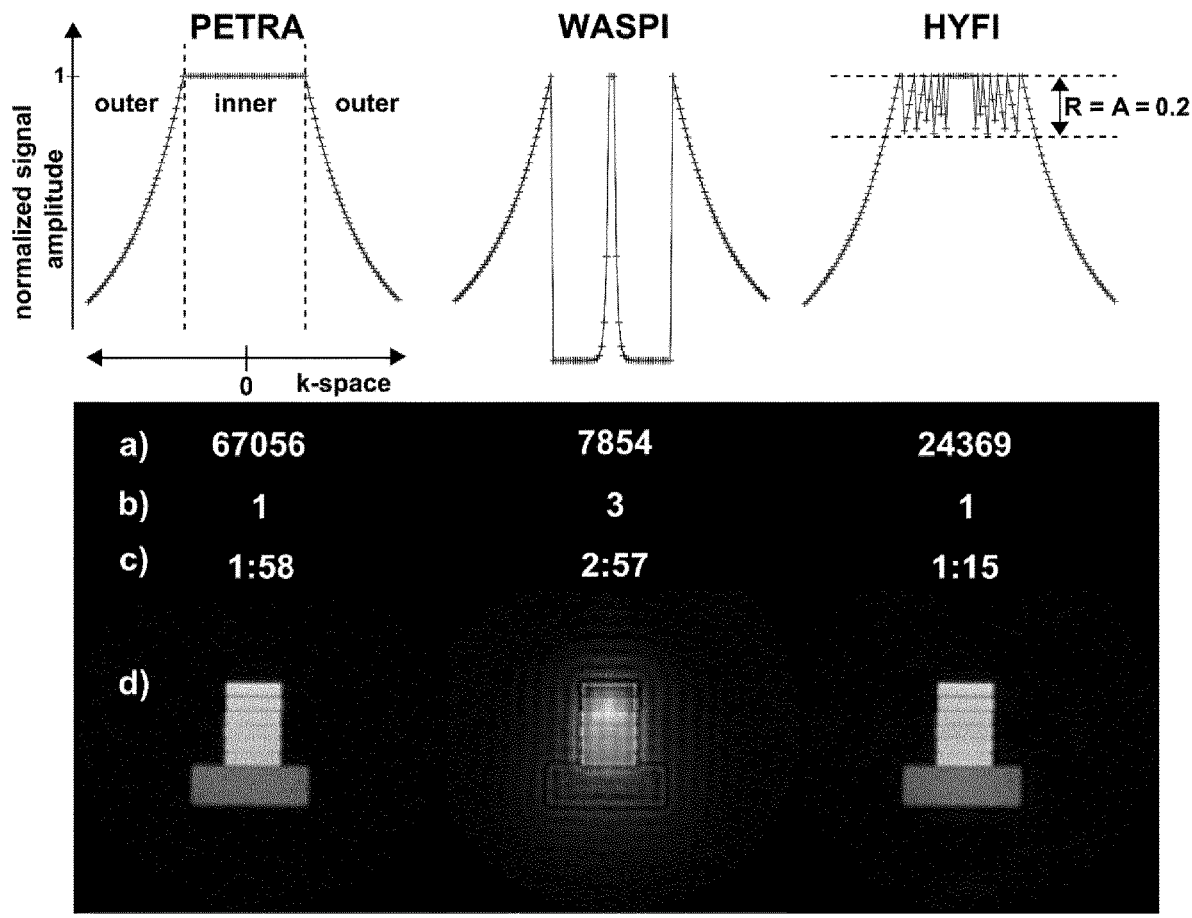
FIG. 7 shows a comparison of magnetic resonance imaging acquired with PETRA (left column), WASPI (middle column) and HYFI (right column).

A comparison of magnetic resonance imaging acquired with PETRA (state of the art), WASPI (state of the art) and HYFI (present invention) is shown in FIG. 7. Magnetic resonance imaging was performed with PETRA (equivalent to HYFI with A=0), WASPI (equivalent to HYFI with A=1) and HYFI (A=0.2).

First Row: 1D representations of the signal T2-weighting in k-space. The signal amplitude in the outer k-space region is exponentially decaying and equivalent in all techniques. However, the acquisition of the inner k-space region is specific to each technique. In PETRA, the signal is acquired point by point at a constant time following the spin excitation leading to a constant T2-weighting in the inner k-space region. In WASPI, the inner k-space region is read out radially with a reduced gradient strength causing stronger signal decay and amplitude jumps at the border separating inner and outer k-space regions. In HYFI, the inner k-space region is split into several sub-regions: a core surrounded by shells. The core is read out single-pointwise similarly to PETRA. The shells are read out radially leading exponential decay of the signal amplitude.

Second Row:
a) Number of spin excitations required for the acquisition of the inner k-space region.

b) Repetition time (time separating two spin excitations) in milliseconds.
c) Total scan duration (min:sec). Note: because of the slow acquisition of the inner k-space region, the repetition time of WASPI was increased to 3 milliseconds causing a strong increase in scan time despite the lower number of required excitations.
d) Images. The sample consists of a stack of erasers (T2≈300 μs) standing on a hockey puck (T2≈100 us). In WASPI, the large amplitude jumps in k-space T2-weighting lead to strong artifacts in the image. HYFI offers similar image quality than PETRA with reduced scan time.

Additional Scanning Parameters:
$\Delta t_0$=100 μs, $k_{gap}$=25 Nyquist dwells, imaging bandwidth=250 kHz, duration of excitation pulse=2 μs

REFERENCES

[1] Froidevaux, R. et al. (2017), Filling the dead-time gap in zero echo time MRI: Principles compared. Magn Reson Med. 2017 Aug. 30. doi: 10.1002/mrm.26875.
[2] Wu Y, Dai G, Ackerman J L, Hrovat M I, Glimcher M J, Snyder B D, Nazarian A, Chesler D a. Water- and fat-suppressed proton projection MRI (WASPI) of rat femur bone. Magn Reson Med 2007; 57:554-67.
[3] Grodzki D M, Jakob P M, Heismann B. Ultrashort echo time imaging using pointwise encoding time reduction with radial acquisition (PETRA). Magn Reson Med 2012; 67:510-8.
[4] Weiger M, Pruessmann K P. MRI with Zero Echo Time. eMagRes 2012; 1:311-22.
[5] Froidevaux R, Weiger M, Rösler M B, Wilm B, Hennel F, Luechinger R, Dietrich B E, Reber J, Pruessmann K P. Ultra-high-bandwidth, high-resolution MRI of fast relaxing spins Shot-T2 MRI: requirements High resolution. Proc 26th Annu Meet ISMRM, Honolulu 2017:4037.

The invention claimed is:

1. A method for generating an image data set of an image area located in a measurement volume of a magnetic resonance system, the magnetic resonance system comprising a gradient system and an RF transmission/reception system, the method comprising:
reading out k-space corresponding to the imaging area, by:
(a) activating a frequency encoding gradient in a predetermined spatial direction and with a predetermined strength $G_0$ via said gradient system,
(b) after the activated frequency encoding gradient achieves its strength $G_0$, radiating a non-slice-selective RF excitation pulse via said RF transmission/reception system,
(c) after a transmit-receive switch time $\Delta t_{TR}$ following the radiated excitation pulse, acquiring FID signals with said RF transmission/reception system and storing said FID signals as raw data points in k-space along a radial k-space trajectory that is predetermined by the direction and strength $G_0$ of the frequency encoding gradient,
(d) repeating (a) through (c) with respectively different frequency encoding gradient directions in each repetition until k-space corresponding to the image area is read out in an outer region of k-space along radial k-space trajectories, said radial k-space trajectories each having a radially innermost limit $k_{gap}$ which depends on said switch time $\Delta t_{TR}$,
(e) reading out a remainder of k-space that corresponds to the imaging area, said remainder being an inner region of k-space not being filled by said first region and including at least a center of k-space, in a read out procedure that is different from (a) through (d), and storing all data points read out in (d) and (e); and
reconstructing image data from the read out data points in k-space by implementing a reconstruction algorithm;
wherein
the inner k-space region is subdivided into a core region and at least one radially adjacent shell region with raw data points in the core region being acquired as Cartesian raw data, and raw data points in the shell region (S) being acquired along radial k-space trajectories using a gradient strength G that is smaller than the gradient strength $G_0$.

2. The method according to claim 1, wherein the boundary $k_{gap}$ subdividing the inner and outer k-space regions is given by the product of bandwidth BW and dead time $\Delta t_0$, wherein the dead time $\Delta t_0$ is given by $\Delta t_{RF}$, which is a part of the RF pulse plus the transmit-receive switch time $\Delta t_{TR}$.

3. The method according to claim 1, wherein the core region has an outer limit $k_{core}$ given by:

$$k_{core} = \frac{\Delta t_0}{\Delta t} \cdot s_{min}$$

wherein
the dead time $\Delta t_0$ is given by $\Delta t_{RF}$, which is a part of the RF pulse plus the transmit-receive switch time $\Delta t_{TR}$,
the allowed acquisition duration $\Delta t$ is given by $-T_2 \ln(1-A)$ wherein A is an amplitude parameter selected between 0 and 1,
the minimum shell thickness $s_{Min}$ is selected to be between 0.1 and 10.

4. The method according to claim 1, wherein the shell region comprises at least two shell regions ($S_1, S_2, \ldots$), each shell region $S_i$ having a shell thickness $s_i$ given by $$s_i = \frac{\Delta t}{\Delta t_0} \cdot k_{in}$$

wherein
dead time $\Delta t_0$ is given by $\Delta t_{RF}$, which is a part of an RF pulse plus the transmit-receive switch time $\Delta t_{TR}$, and
allowed acquisition duration $\Delta t$ is given by $-T_2 \ln(1-A)$ wherein A is an amplitude parameter selected between 0 and 1,
each shell region having an inner radius $k_{in}$ defined by the thickness of the next radially inward core or shell region.

5. The method according to claim 1, wherein the reconstruction algorithm comprises a Fourier transformation of the data points.

6. The method according to claim 2, wherein $\Delta t_{RF}$ is half of the RF pulse for symmetric RF pulses.

7. The method according to claim 3, wherein $\Delta t_{RF}$ is half of the RF pulse for symmetric RF pulses.

8. The method according to claim 3, wherein the minimum shell thickness $s_{Min}$ is between 0.5 and 2.

9. The method according to claim 3, wherein the minimum shell thickness $s_{Min}$ is about 1.

10. The method according to claim 2, wherein the shell region comprises at least two shell regions ($S_1, S_2, \ldots$), each shell region S, having a shell thickness $s_i$ given by $$s_i = \frac{\Delta t}{\Delta t_0} \cdot k_{in}$$

wherein allowed acquisition duration $\Delta t$ is given by $-T_2 \ln(1-A)$, wherein A is an amplitude parameter selected between 0 and 1, each shell region having an inner radius $k_{in}$ defined by the thickness of the next radially inward core or shell region.

11. The method according to claim 3, wherein the shell region comprises at least two shell regions ($S_1, S_2, \ldots$), each shell region S, having a shell thickness $s_i$ given by $$s_i = \frac{\Delta t}{\Delta t_0} \cdot k_{in}$$

each shell region having an inner radius $k_{in}$ defined by the thickness of the next radially inward core or shell region.

12. The method according to claim 2, wherein the reconstruction algorithm comprises a Fourier transformation of the data points.

13. The method according to claim 3, wherein the reconstruction algorithm comprises a Fourier transformation of the data points.

14. The method according to claim 4, wherein the reconstruction algorithm comprises a Fourier transformation of the data points.

* * * * *